United States Patent
Hataoka (10) Patent No.: US 8,980,645 B2
(45) Date of Patent: *Mar. 17, 2015

(54) METHOD FOR IMMOBILIZING PROTEIN A ON A SELF-ASSEMBLED MONOLAYER

(75) Inventor: Yukari Hataoka, Osaka (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 56 days.

This patent is subject to a terminal disclaimer.

(21) Appl. No.: 13/483,840

(22) Filed: May 30, 2012

(65) Prior Publication Data

US 2012/0238036 A1   Sep. 20, 2012

Related U.S. Application Data

(63) Continuation of application No. PCT/JP2011/000268, filed on Jan. 19, 2011.

(30) Foreign Application Priority Data

Jan. 25, 2010  (JP) ................................ 2010-012710

(51) Int. Cl.
  *G01N 33/547*  (2006.01)
  *G01N 33/544*  (2006.01)
  (Continued)

(52) U.S. Cl.
  CPC .......... *G01N 33/54353* (2013.01); *C07K 14/31* (2013.01); *G01N 33/54393* (2013.01); *C07K 14/195* (2013.01); *G01N 2610/00* (2013.01)
  USPC .......................................... 436/532; 436/528

(58) Field of Classification Search
  CPC ............... G01N 2610/00; G01N 33/54353; C07K 14/31; C07K 2319/20; C07K 1/1075; C07K 14/1075; A61K 2039/625
  See application file for complete search history.

(56) References Cited

U.S. PATENT DOCUMENTS

| 5,137,804 A | 8/1992 | Greene et al. |
| 5,391,478 A | 2/1995 | Greene et al. |

(Continued)

FOREIGN PATENT DOCUMENTS

| EP | 0 865 197 A2 | 9/1998 |
| EP | 908957 A2 | 4/1999 |

(Continued)

OTHER PUBLICATIONS

International Search Report issued in International Patent Application No. PCT/JP2011/000268, mailed Apr. 5, 2011.

(Continued)

*Primary Examiner* — Shafiqul Haq
(74) *Attorney, Agent, or Firm* — McDermott Will & Emery LLP

(57) ABSTRACT

The object of the present invention is to provide a method for increasing an amount of Protein A to be immobilized on the self-assembled monolayer. Immobilizing Protein A to the self-assembled monolayer through the structure represented following formula (II) obviates the object.

[Chem. 2]

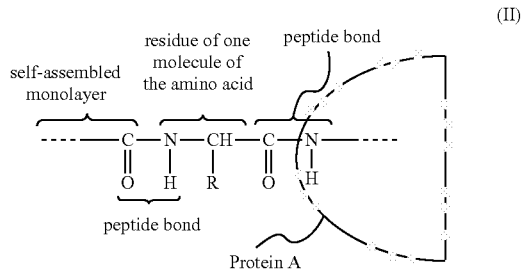

9 Claims, 3 Drawing Sheets

(51) Int. Cl.
  *G01N 33/543* (2006.01)
  *C07K 14/31* (2006.01)
  *C07K 14/195* (2006.01)

(56) References Cited

U.S. PATENT DOCUMENTS

| | | | |
|---|---|---|---|
| 5,969,758 A | 10/1999 | Sauer et al. |
| 6,037,577 A | 3/2000 | Tanaka et al. |
| 6,061,093 A | 5/2000 | Yonemoto |
| 6,115,066 A | 9/2000 | Gowda et al. |
| 6,235,535 B1 | 5/2001 | Keinanen et al. |
| 6,344,877 B1 | 2/2002 | Gowda et al. |
| 6,366,321 B1 | 4/2002 | Yonemoto |
| 6,406,921 B1 | 6/2002 | Wagner et al. |
| 6,475,808 B1 | 11/2002 | Wagner et al. |
| 6,576,478 B1 | 6/2003 | Wagner et al. |
| 6,582,969 B1 | 6/2003 | Wagner et al. |
| 6,596,545 B1 | 7/2003 | Wagner et al. |
| 6,650,369 B2 | 11/2003 | Koizumi et al. |
| 6,682,942 B1 | 1/2004 | Wagner et al. |
| 6,791,613 B2 | 9/2004 | Shinohara et al. |
| 7,030,922 B2 | 4/2006 | Sakuragi |
| 7,110,030 B1 | 9/2006 | Kochi et al. |
| 7,116,365 B1 | 10/2006 | Ueno et al. |
| 7,277,130 B2 | 10/2007 | Korthout et al. |
| 7,283,168 B2 | 10/2007 | Watanabe |
| 7,317,483 B2 | 1/2008 | Tanimoto |
| 7,375,753 B2 | 5/2008 | Mabuchi |
| 7,714,920 B2 | 5/2010 | Inagaki et al. |
| 2002/0110932 A1 | 8/2002 | Wagner et al. |
| 2002/0115225 A1 | 8/2002 | Wagner et al. |
| 2003/0137594 A1 | 7/2003 | Koizumi et al. |
| 2003/0138973 A1 | 7/2003 | Wagner et al. |
| 2004/0027471 A1 | 2/2004 | Koseki et al. |
| 2004/0175300 A1 | 9/2004 | Indermuhle et al. |
| 2004/0197931 A1 | 10/2004 | Indermuhle et al. |
| 2004/0251396 A1 | 12/2004 | Koyama |
| 2005/0083408 A1 | 4/2005 | Mabuchi |
| 2005/0128326 A1 | 6/2005 | Korthout et al. |
| 2005/0281816 A1 | 12/2005 | Lamping et al. |
| 2006/0001751 A1 | 1/2006 | Abe et al. |
| 2009/0011952 A1 | 1/2009 | Gau |
| 2009/0042744 A1 | 2/2009 | Wagner et al. |
| 2009/0047685 A1 | 2/2009 | Kohno et al. |
| 2009/0047695 A1 | 2/2009 | Wagner et al. |
| 2009/0202580 A1 | 8/2009 | Uggeri et al. |
| 2009/0325262 A1 | 12/2009 | Hodneland et al. |
| 2010/0113476 A1 | 5/2010 | Chen et al. |
| 2010/0233827 A1 | 9/2010 | Kusaki et al. |
| 2012/0238036 A1 | 9/2012 | Hataoka |
| 2013/0029364 A1 | 1/2013 | Hataoka |

FOREIGN PATENT DOCUMENTS

| | | | |
|---|---|---|---|
| GB | 2 347 212 A | 8/2000 |
| JP | 01-209370 A | 8/1989 |
| JP | 07-113637 B | 12/1995 |
| JP | 9-247537 A | 9/1997 |
| JP | 10-93066 A | 4/1998 |
| JP | 11-014627 A | 1/1999 |
| JP | 11-112018 A | 4/1999 |
| JP | 2000-515965 A | 11/2000 |
| JP | 2001-045375 A | 2/2001 |
| JP | 2001-305139 A | 10/2001 |
| JP | 2002-511215 A | 4/2002 |
| JP | 2002-520618 | 7/2002 |
| JP | 2002-520618 A | 7/2002 |
| JP | 2002-520621 A | 7/2002 |
| JP | 2002-237584 A | 8/2002 |
| JP | 2003-230055 A | 8/2003 |
| JP | 2005-509737 A | 4/2005 |
| JP | 2006-502719 A | 1/2006 |
| JP | 2006-166837 A | 6/2006 |
| JP | 2006-208012 A | 8/2006 |
| JP | 2006-266707 | 10/2006 |
| JP | 2006-266707 A | 10/2006 |
| JP | 2007-528850 A | 10/2007 |
| JP | 2007-298334 A | 11/2007 |
| JP | 2009-222401 A | 10/2009 |
| JP | 2009-541259 A | 11/2009 |
| JP | 2010-117140 A | 5/2010 |
| JP | 2010-237191 A | 10/2010 |
| JP | 2010-532475 A | 10/2010 |
| WO | 89/11100 A1 | 11/1989 |
| WO | 98/00714 A1 | 1/1998 |
| WO | 98/56170 A1 | 12/1998 |
| WO | 00/04382 A1 | 1/2000 |
| WO | 00/04390 A2 | 1/2000 |
| WO | WO 00/04382 | 1/2000 |
| WO | 03/018854 A2 | 3/2003 |
| WO | 03/069897 A1 | 8/2003 |
| WO | 2005/018413 A2 | 3/2005 |
| WO | 2007/063616 A1 | 6/2007 |
| WO | 2009/005567 A1 | 1/2009 |
| WO | 2011/089903 A1 | 7/2011 |
| WO | 2012/029202 A1 | 3/2012 |
| WO | 2012/053138 A1 | 4/2012 |
| WO | 2012/168988 A1 | 12/2012 |
| WO | 2013/005269 A1 | 1/2013 |

OTHER PUBLICATIONS

Gooding et al., "Amperometric biosensor with enzyme amplification fabricated using self-assembled monolayers of alkanethiols: the influence of the spatial distribution of the enzymes", Electrochemistry Communications, vol. 2, No. 4, Apr. 1, 2000, pp. 217-221.

International Search Report issued in International Application No. PCT/JP2011/004127 issued on Aug. 16, 2011.

International Search Report mailed Mar. 29, 2011 issued in corresponding International Application No. PCT/JP2011/001185.

International Search Report issued in International Patent Application No. PCT/JP2011/007239 dated Feb. 7, 2012.

International Search Report issued in International Application No. PCT/JP2011/007238 with Date of mailing Feb. 7, 2012.

Besselink et al., "N-hydroxysuccinimide-activated glycine-sepharose," Applied Biochemistry and Biotechnology 2003, vol. 43, pp. 227-246.

Diamandis et al., "The biotin-(strept)avidin system: principles and applications in biotechnology," Clin. Chem. 1991, vol. 37, No. 5, pp. 625-636.

Non-Final Office Action issued in U.S. Appl. No. 13/629,121 dated Jan. 4, 2013.

Non-Final Office Action issued in U.S. Appl. No. 13/629,121 dated Mar. 5, 2013.

Non-Final Office Action issued in U.S. Appl. No. 13/629,121 dated Sep. 16, 2013.

International Search Report issued in International Application No. PCT/JP2011/005037 with Date of mailing Oct. 11, 2011, with English Translation.

Kondo et al., "Plasma-Assisted Immobilization of Heparin onto Low-Density Polyethylene Surface," Chem. Pharm. Bull., 2008, vol. 56, No. 7, p. 921-925.

Shriver-Lake et al., Antibody Immobilization Using Heterobifunctional Crosslinkers, Biosensors & Bioelectronics, 1997, vol. 12, No. 11, p. 1101-1106.

English translation of Chinese Search Report issued in Chinese Application No. 201180037848.6 dated Mar. 3, 2014.

Fig. 2

METHOD FOR IMMOBILIZING PROTEIN A ON A SELF-ASSEMBLED MONOLAYER

RELATED APPLICATIONS

This application is a continuation of International Application No. PCT/JP2011/000268, filed on Jan. 19, 2011, which in turn claims the benefit of Japanese Application No. 2010-012710, filed on Jan. 25, 2010, the disclosures of which Applications are incorporated by reference herein.

TECHNICAL FIELD

The present invention relates to a method for immobilizing Protein A on a self-assembled monolayer.

BACKGROUND ART

A biosensor is used to detect or quantify a target substance, namely an antigen, contained in a sample. A high affinity between an antigen and an antibody and a high affinity between Protein A and an antibody may be used in the biosensor. Specifically, Protein A is immobilized on the biosensor. Furthermore, an antibody is immobilized on the Protein A. When the antigen is supplied to the biosensor, the antigen is immobilized on the biosensor due to the high affinity between the antigen and the antibody.

Figure 2:
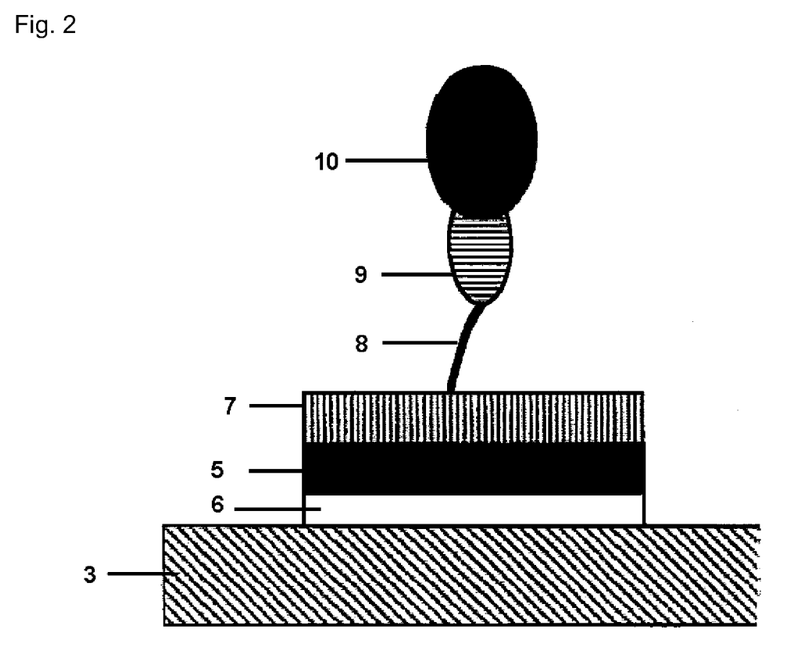
FIG. 2 is FIG. 7 of Patent Document 1.

Patent Document 1 discloses a prior biosensor utilizing the high affinity between Protein A and biotin. FIG. 2 shows a biosensor disclosed in FIG. 7 of the Patent Document 1.

According to the description regarding FIG. 7 of the Patent Document 1, the biosensor is used for screening an activity of a living molecule. The biosensor comprises a monolayer 7, an affinity tag 8, an adaptor molecule 9, and a protein 10. The monolayer 7 is composed of a self-assembled monolayer represented by chemical formula: X—R—Y (see Page 24 lines 23-26, Page 25 lines 3-20, Page 25 line 27-Page 26 line 13, and Page 26 lines 14-22 of Patent Document 1). Examples of X, R, and Y are HS—, an alkane, and a carboxyl group, respectively (see Page 25 lines 3-20, Page 25 line 27-Page 26 line 13, and Page 28 lines 21-23 of Patent Document 1).

CITATION LIST

Patent Literature

PTL 1: WO00/04382, which corresponds to Japanese Laid-Open Patent Publication No. 2002-520618 (see paragraph [0080], [0082], [0084], [0085], [0095] and [0109], [0119])

SUMMARY OF INVENTION

Technical Problem

In order to improve the detection sensitivity or the quantification accuracy of the target substance, it is required to increase an amount of Protein A to be immobilized on the biosensor.

The inventor of the present invention has discovered that the amount of immobilized Protein A per unit area was significantly increased by binding one molecule of the amino acid to a self-assembled monolayer and then immobilizing Protein A. The invention has been provided on the basis of the discovery.

The purpose of the present invention is to provide a method for increasing an amount of Protein A to be immobilized on the self-assembled monolayer, and a sensor with the protein A immobilized with the same method.

Solution to Problem

The following items A1 to C6 solve the above problem(s).

A1: A method for immobilizing a Protein A on a self-assembled monolayer, comprising the following step (a) and step (b) in this order:

a step (a) of preparing a substrate comprising the one molecule of the amino acid and the self-assembled monolayer, wherein the one molecule of the amino acid is bound to the self-assembled monolayer through a peptide bond represented by the following chemical formula (I):

[Chem. 1]

(I)

(wherein R represents a side chain of one molecule of the amino acid)

the one molecule of the amino acid is selected from the nineteen kinds of the amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, and valine, and a step (b) of supplying the Protein A to the substrate to form a peptide bond represented by the following chemical formula (II) as a result of reaction between carboxyl group of the one molecule of the amino acid and amino group of the Protein A.

[Chem. 2]

(II)

(wherein R represents a side chain of one molecule of the amino acid)

A2: A method according to the A1, wherein the step (a) comprises the following step (a1) and step (a2) in this order:

a step (a1) of preparing a substrate comprising a self-assembled monolayer on the surface thereof, the self-assembled monolayer having a carboxyl group at its one end, and a step (a2) of supplying the one molecule of the amino acid to form a peptide bond represented by the chemical formula

(I) as a result of reaction between carboxyl group at one end of the self-assembled monolayer and amino group of the one molecule of the amino acid.

A3: A method according to the A1, further comprising the following step (ab) between the step (a) and the step (b):
a step (ab) of activating the carboxyl group of the one molecule of the amino acid with a mixture of N-Hydroxysuccinimide and 1-ethyl-3-(3-dimethylaminopropyl)carbodiimide hydrochloride.

A4: A method according to the A2, further comprising the following step (a1a) between the step (a1) and the step (a2):
a step (a1a) of activating the carboxyl group of the self-assembled monolayer with a mixture of N-Hydroxysuccinimide and 1-ethyl-3-(3-dimethylaminopropyl)carbodiimide hydrochloride.

A5: A method according to the A1, wherein the chemical formula (II) is represented by the following chemical formula (III).

[Chem. 3]

(III)

(wherein R represents a side chain of the one molecule of the amino acid)

A6: A method according to the A1, wherein the one molecule of the amino acid is selected from the group consisting of cysteine, lysine, histidine, phenylalanine, tyrosine, glycine, asparagine, methionine, serine, tryptophan, leucine, glutamine, alanine, isoleucine, threonine, proline, glutamate, and aspartate.

A7: A method according to the A1, wherein the one molecule of the amino acid is selected from the group consisting of cysteine, lysine, histidine, phenylalanine, tyrosine, glycine, asparagine, methionine, serine, tryptophan, leucine, glutamine, alanine, isoleucine, and threonine.

A8: A method according to the A1, wherein the one molecule of the amino acid is selected from the group consisting of cysteine, lysine, histidine, phenylalanine, tyrosine, glycine, asparagine, methionine, serine, and tryptophan.

A9: A method according to the A1, wherein the one molecule of the amino acid is selected from the group consisting of cysteine, lysine, histidine, phenylalanine, and glycine.

B1: A sensor comprising a self-assembled monolayer, a one molecule of the amino acid, and a Protein A, wherein,
the one molecule of the amino acid is interposed between the self-assembled monolayer and the Protein A,
the Protein A is bound to the self-assembled monolayer through two peptide bonds represented by the following chemical formula (II),

[Chem. 2]

(II)

(wherein R represents a side chain of one molecule of the amino acid)
the one molecule of the amino acid is selected from the nineteen kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, and valine.

B2: A method according to the B1, wherein the chemical formula (II) is represented by the following chemical formula (III).

[Chem. 3]

(III)

(wherein R represents a side chain of one molecule of the amino acid)

B3: A sensor according to the B1, wherein the one molecule of the amino acid is selected from the group consisting of cysteine, lysine, histidine, phenylalanine, tyrosine, glycine, asparagine, methionine, serine, tryptophan, leucine, glutamine, alanine, isoleucine, threonine, proline, glutamate, and aspartate.

B4: A sensor according to the B1, wherein the one molecule of the amino acid is selected from the group consisting of cysteine, lysine, histidine, phenylalanine, tyrosine, glycine, asparagine, methionine, serine, tryptophan, leucine, glutamine, alanine, isoleucine, and threonine.

B5: A sensor according to the B1, wherein the one molecule of the amino acid is selected from the group consisting of cysteine, lysine, histidine, phenylalanine, tyrosine, glycine, asparagine, methionine, serine, and tryptophan.

B6: A sensor according to the B1, wherein the one molecule of the amino acid is selected from the group consisting of cysteine, lysine, histidine, phenylalanine, and glycine.

C1: A method for detecting or quantifying a target substance contained in a sample with a sensor, comprising the following steps (a) to (c) in this order, a step (a) of preparing the sensor comprising a self-assembled monolayer, a one molecule of the amino acid, a Protein A, and an antibody, wherein, the one molecule of the amino acid is interposed between the self-assembled monolayer and the Protein A, the Protein A is interposed between the antibody and the one molecule of the amino acid, the antibody is bound specifically to the target substance, the Protein A is bound to the self-assembled monolayer through two peptide bonds represented by the following chemical formula (II),

[Chem. 2]

(II)

(wherein R represents a side chain of one molecule of the amino acid)

the one molecule of the amino acid is selected from the nineteen kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, and valine, a step (b) of supplying the sample to the sensor to cause the target substance to be bound to Protein A, and a step (c) of detecting or quantifying the target substance contained in the sample from the captured target substance or the amount thereof.

C2: A method according to the C1, wherein the chemical formula (II) is represented by the following chemical formula (III).

[Chem. 3]

(III)

(wherein R represents a side chain of one molecule of the amino acid)

C3: A method according to the C1, wherein the one molecule of the amino acid is selected from the group consisting of cysteine, lysine, histidine, phenylalanine, tyrosine, glycine, asparagine, methionine, serine, tryptophan, leucine, glutamine, alanine, isoleucine, threonine, proline, glutamate, and aspartate.

C4: A method according to the C1, wherein the one molecule of the amino acid is selected from the group consisting of cysteine, lysine, histidine, phenylalanine, tyrosine, glycine, asparagine, methionine, serine, tryptophan, leucine, glutamine, alanine, isoleucine, and threonine.

C5: A method according to the C1, wherein the one molecule of the amino acid is selected from the group consisting of cysteine, lysine, histidine, phenylalanine, tyrosine, glycine, asparagine, methionine, serine, and tryptophan.

C6: A method according to the C1, wherein the one molecule of the amino acid is selected from the group consisting of cysteine, lysine, histidine, phenylalanine, and glycine.

Advantageous Effect of Invention

The present invention achieves extreme increase of the amount of the protein A to be immobilized per unit area.

DESCRIPTION OF EMBODIMENTS

The embodiment of the present invention is described below with reference to FIG. 1.

Embodiment 1

Figure 1:
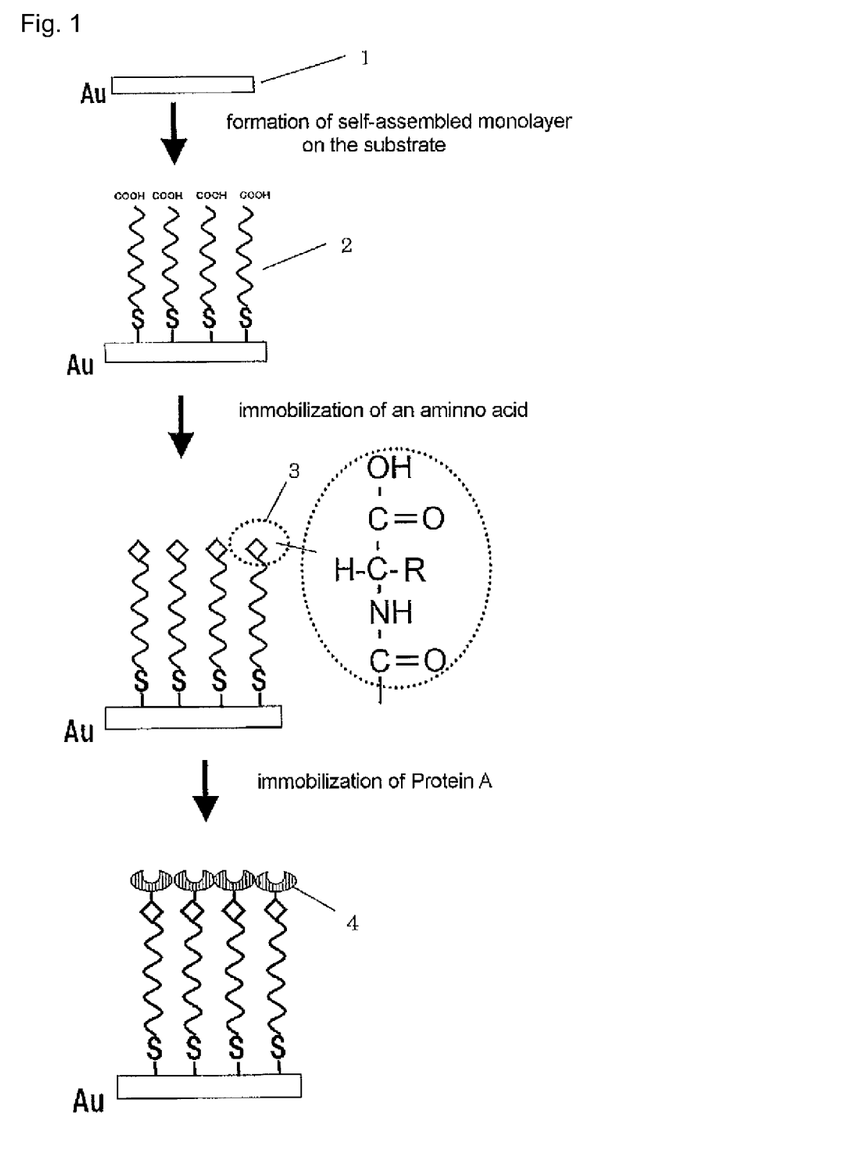
FIG. 1 shows a schematic view of a method according to the present invention.

FIG. 1 shows a method according to the present invention for immobilizing a Protein A on a self-assembled monolayer.

Preferably, a substrate 1 is a gold substrate. An example of the gold substrate is a substrate comprising gold on its surface. Specifically, the gold substrate may be a formed by sputtering gold on the surface of glass, plastic, or silicon dioxide (SiO2).

First, the substrate 1 is immersed into a solvent containing an alkanethiol. Preferably, the substrate is washed before the immersing. The alkanethiol has a carboxyl group at the end thereof. As the alkanethiol, a primary alkanethiol having carbon number within the range from 6 to 18 can be employed preferably. Thus, a self-assembled monolayer 2 is formed on the substrate 1.

A preferred concentration of the alkanethiol is approximately 1 to 10 mM. The solvent is not limited as long as it dissolves the alkanethiol. Examples of the preferred solvent are ethanol, DMSO (dimethyl sulfoxide), and dioxane. The preferred immersing period is approximately 12 to 48 hours.

Next, an amino acid 3 is supplied to the self-assembled monolayer 2. The carboxyl group (—COOH) which locates at the top end of the self-assembled monolayer 2 reacts with an amino group (—NH2) of the amino acid 3 to form a peptide bond represented by the following chemical formula (I).

[Chem. 1]

(I)

(wherein R represents side chain of one molecule of the amino acid)

In the chemical formula (I), the one molecule of the amino acid 3 binds to the self-assembled monolayer 2.

The amino acid 3 is selected from nineteen kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, and valine. Namely, in the chemical formula (I), R is the side chain of these nineteen kinds of amino acids.

when amino acid 3 is supplied to the self-assembled monolayer 2, equal to or more than two kinds of amino acids may be supplied simultaneously. Namely, when a solution containing the amino acid 3 is supplied to the self-assembled monolayer 2, the solution may contain equal to or more than two kind of the amino acids 3. In light of uniform bind of Protein A to the amino acid 3, which is described later, it is preferred that the solution contains a sole kind of amino acid.

As described later in the examples, arginine is not utilized as the amino acid 3. It is because an immobilization amount in case where arginine is supplied is lower than an immobilization amount in case where no amino acid is supplied. In case where no amino acid is supplied, a carboxyl group located at the end of the self-assembled monolayer 2 directly binds to Protein A.

Subsequently, Protein A 4 is supplied. The 5'-terminal amino group of the Protein A 4 reacts with the carboxyl group of the amino acid 3. The amino group of the lysine contained in the Protein A also reacts with the carboxyl group of the amino acid 3. Thus, two peptide bonds represented in following chemical formula (II) are formed to obtain a sensor.

[Chem. 2]

(II)

(wherein R represents a side chain of one molecule of the amino acid)

One molecule of the Protein A 4 has only one 5'-terminal, whereas one molecule of the Protein A 4 has a lot of lysine group. Therefore, almost all of the chemical formula (II) is related particularly by the following chemical formula (III).

[Chem. 3]

(III)

(wherein R represents a side chain of one molecule of the amino acid)

The obtained sensor is used for detecting or quantifying target substance contained in sample.

Specifically, an antibody which can bind the target substance specifically is supplied to the sensor to bind the antibody to the Protein A. Namely, the antibody is captured by the Protein A. Subsequently, the sample is supplied to the sensor to cause target substance, which is an antigen, contained in the sample to bind to the antibody. Needless to say, the antibody is bound specifically to the target substance.

Finally, with use of an ordinal analysis method such as Surface Plasmon Resonance (SPR) analysis method, the target substance is detected or quantified. Another analysis method such as Quarts Crystal Microbalance (QCM) may be used.

EXAMPLE

The following examples and a comparative example describe the present invention in more detail.

Comparative Example 1

Figure 3:
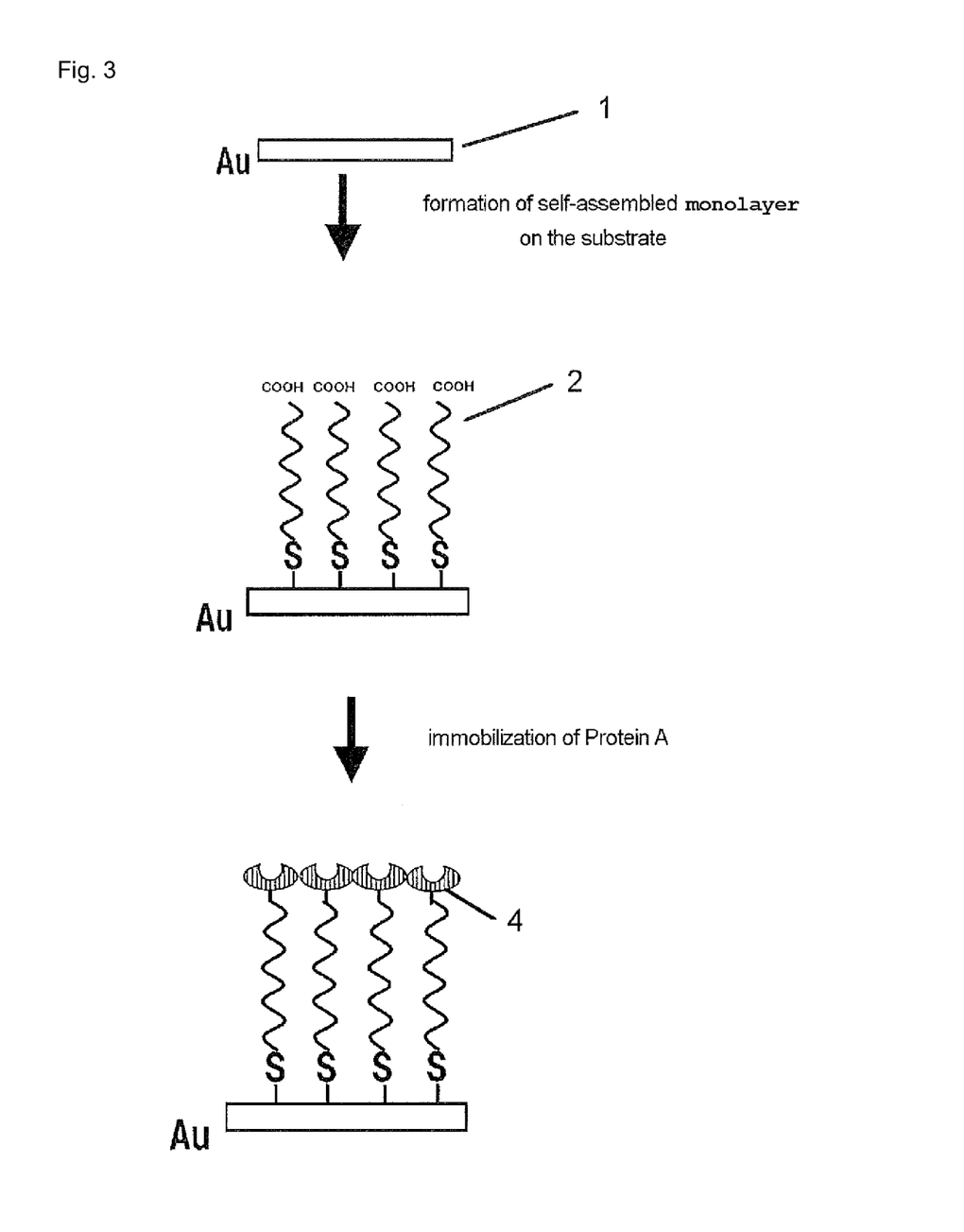
FIG. 3 shows a schematic view of a method according to the prior art.

As shown in FIG. 3, a Protein A was bound directly to a carboxyl group located at the top end of self-assembled alkanethiol formed on the gold surface with an amide coupling reaction to immobilize the Protein A. The procedure and the results were described below.

(Preparation of a Sample Solution)

A sample solution of 16-Mercaptohexadecanoic acid with final concentration of 10 mM was prepared. The solvent thereof was ethanol.

(Formation of a Self-Assembled Monolayer)

A gold substrate (available from GE healthcare company, BR-1004-05) in which gold was vapor-deposited on glass was used as a substrate 1. The substrate 1 was washed for ten minutes with a piranha solution containing concentrated sulfuric acid and 30% hydrogen peroxide water. The volume ratio of the concentrated sulfuric acid to the 30% hydrogen peroxide water which are consisting of the piraniha solution was 3:1.

Subsequently, the gold substrate was immersed in the sample solution for 18 hours to form a self-assembled monolayer on the surface of the gold substrate. Finally, the substrate 1 was washed with pure water and dried.

(Immobilization of Protein A)

Protein A was bound to the carboxyl group located at the top end of the 16-Mercaptohexadecanoic acid which was forming the self-assembled monolayer to immobilize the Protein A.

Specifically, the carboxyl acid group located at the top end of the 16-Mercaptohexadecanoic acid was activated with use of 35 micro L of a mixture of 0.1M NHS (N-Hydroxysuccinimide) and 0.4M EDC (1-ethyl-3-(3-dimethylaminopropyl) carbodiimide hydrochloride). Subsequently, 35 micro L of Protein A (40 ug/ml) was added at the flow rate of 5 micro L/minute. Thus, the carboxyl group of the 16-Mercaptohexadecanoic acid was coupled with the amino group of the Protein A.

Example 1

Experiment was conducted similarly to the comparative example except that glycine was supplied as the one molecule of the amino acid between the formation of self-assembled monolayer and the immobilization of the Protein A. The procedure and the results are described below.

(Immobilization of Amino Acid (Glycine))

Glycine was bound with the carboxyl group located at top end of the 16-Mercaptohexadecanoic acid which formed the self-assembled monolayer 2 to immobilize the glycine.

Specifically, after the carboxyl group had activated similar to the Comparative Example 1, 35 micro L of 0.1M glycine (pH: 8.9) was added at the flow rate of 5 micro L/minute. Thus, the carboxyl group of 16-Mercaptohexadecanoic acid was coupled with the amino group of the glycine.

(Immobilization of Protein A)

Subsequently, Protein A was bound to the carboxyl group of the glycine, to immobilize Protein A. Specifically, after the carboxyl group of the glycine was activated similar to the above, 35 micro L of Protein A (concentration: 250 micro gram/ml) was added at the flow rate of 5 micro L/minute. Thus, the carboxyl group was coupled with the 5'-terminal amino acid of the Protein A or the amino group of the lysine contained in the Protein A.

(Comparison of the Immobilization Amounts)

The immobilization amounts in the example 1 and in the comparative example 1 were measured with the use of an SPR device Biacore 3000 (available from GE healthcare company).

The term "immobilization amount" means the amount of the Protein A immobilized per unit area.

The ratio of the immobilization amount measured in the example 1 to that of measured in the comparative example 1 was approximately 8:1.

Examples 2-19

Threonine, methionine, isoleucine, proline, serine, glutamine, asparagine, phenylalanine, tryptophan, cysteine, histidine, alanine, lysine, leucine, glutamate, valine, aspartate, arginine, and tyrosine were supplied respectively instead of glycine. The respective immobilization amounts were measured similar to the example 1. These amino acids are twenty kinds of natural amino acid, provided that arginine is excluded. Table 1 shows the measured immobilization amounts.

Comparative Example 2

Experiment was conducted similarly to the Example 1 except that arginine was supplied instead of glycine as one molecule of the amino acid, the immobilization amount was measured.

TABLE 1

|  | amino acid | amount |
| --- | --- | --- |
| Example 11 | Cysteine | 185 |
| Example 14 | Lysine | 147 |
| Example 12 | Histidine | 117 |
| Example 9 | Phenylalanine | 112 |
| Example 1 | Glycine | 100 |
| Example 8 | Asparagine | 95 |
| Example 3 | Methionine | 94 |
| Example 6 | Serine | 92 |
| Example 19 | Tyrosine | 87 |
| Example 10 | Tryptophan | 86 |
| Example 15 | Leucine | 80 |
| Example 7 | Glutamine | 76 |
| Example 13 | Alanine | 75 |
| Example 4 | Isoleucine | 57 |
| Example 2 | Threonine | 54 |
| Example 5 | Proline | 42 |
| Example 16 | Glutamate | 33 |
| Example 18 | Aspartate | 25 |
| Example 17 | Valine | 21.7 |
| Comparative Example 2 | Arginine | 6.4 |
| Comparative Example 1 | (None) | 12.7 |

A skilled person would understand the following matters from the table 1. When the nineteen kinds of amino acids, except for arginine, was supplied, the immobilization amounts increase compared to comparative examples. Furthermore, the immobilization amount changes depending on amino acid.

Cysteine, lysine, histidine, phenylalanine, tyrosine, glycine, asparagine, methionine, serine, tryptophan, leucine, glutamine, alanine, isoleucine, threonine, proline, glutamate, and aspartate are preferred, because each measured immobilization amounts is equal to or more than twenty, in a case where one of these amino acids is supplied.

Cysteine, lysine, histidine, phenylalanine, tyrosine, glycine, asparagine, methionine, serine, tryptophan, leucine, glutamine, alanine, isoleucine, and threonine are more preferred, because each measured immobilization amounts is equal to or more than fifty, in a case where one of these amino acids is supplied.

Cysteine, lysine, histidine, phenylalanine, tyrosine, glycine, asparagine, methionine, serine, and tryptophan are furthermore preferred, because each measured immobilization amounts is more than the average value (83.3%), in a case where one of these amino acids is supplied.

Cysteine, lysine, histidine, phenylalanine, and glycine are most preferred, because each measured immobilization amounts is equal to or more than one hundred, in a case where one of these amino acids is supplied.

INDUSTRIAL APPLICABILITY

The present invention achieves extreme increase of the amount of the Protein A to be immobilized per unit area. This allows the sensitivity or the accuracy of the biosensor to be improved. The biosensor may be used for an inspection or a diagnosis which requires the detection or the quantification of an antigen or an antibody contained in the living sample derived from a patient at a clinical practice.

REFERENCE SIGNS LIST

1: Gold substrate
2: Alkanethiol
3: Amino Acid
4: Protein A

The invention claimed is:

1. A method for immobilizing a Protein A on a self-assembled monolayer, comprising the following step (a) and step (b) in this order:
   a step (a) of preparing a substrate comprising immobilization of one molecule of amino acid on the self-assembled monolayer, wherein the one molecule of the amino acid is immobilized to the self-assembled monolayer through a peptide bond represented by the following chemical formula (I):

(I)

wherein R represents a side chain of one molecule of the amino acid; and wherein
the one molecule of the amino acid is selected from the nineteen kinds of the amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, and valine, and
   a step (b) of supplying the Protein A to the substrate to form a peptide bond represented by the following chemical formula (II):

(II)

as a result of reaction between carboxyl group of the one molecule of the amino acid and amino group of the Protein A; wherein R represents a side chain of one molecule of the amino acid.

2. A method according to claim 1, wherein the step (a) comprises the following step (a1) and step (a2) in this order:
   a step (a1) of preparing a substrate comprising a self-assembled monolayer on the surface thereof, the self-assembled monolayer having a carboxyl group at its one end, and
   a step (a2) of supplying the one molecule of the amino acid to form a peptide bond represented by the chemical formula (I) as a result of reaction between carboxyl group at one end of the self-assembled monolayer and amino group of the one molecule of the amino acid.

3. A method according to claim 1, further comprising the following step (ab) between the step (a) and the step (b):
   a step (ab) of activating the carboxyl group of the one molecule of the amino acid with a mixture of N-Hydroxysuccinimide and 1-ethyl-3-(3-dimethylaminopropyl) carbodiimide hydrochloride.

4. A method according to claim 2, further comprising the following step (a1a) between the step (a1) and the step (a2):
   a step (a1a) of activating the carboxyl group of the self-assembled monolayer with a mixture of N-Hydroxysuccinimide and 1-ethyl-3-(3-dimethylaminopropyl)carbodiimide hydrochloride.

5. A method according to claim 1, wherein the chemical formula (II) is represented by the following chemical formula (III):

(III)

wherein R represents a side chain of the one molecule of the amino acid.

6. A method according to claim 1, wherein the one molecule of the amino acid is selected from the group consisting of cysteine, lysine, histidine, phenylalanine, tyrosine, glycine, asparagine, methionine, serine, tryptophan, leucine, glutamine, alanine, isoleucine, threonine, proline, glutamate, and aspartate.

7. A method according to claim 1, wherein the one molecule of the amino acid is selected from the group consisting of cysteine, lysine, histidine, phenylalanine, tyrosine, glycine, asparagine, methionine, serine, tryptophan, leucine, glutamine, alanine, isoleucine, and threonine.

8. A method according to claim 1, wherein the one molecule of the amino acid is selected from the group consisting of cysteine, lysine, histidine, phenylalanine, tyrosine, glycine, asparagine, methionine, serine, and tryptophan.

9. A method according to claim 1, wherein the one molecule of the amino acid is selected from the group consisting of cysteine, lysine, histidine, phenylalanine, and glycine.

* * * * *